United States Patent [19]

Haefele et al.

[11] Patent Number: 4,985,126

[45] Date of Patent: Jan. 15, 1991

[54] APPARATUS AND PROCESS FOR CONTINUOUSLY MONITORING CONCENTRATIONS OF GASEOUS COMPONENTS IN GAS MIXTURES, WITH EXCEPTION OF $O_2$

[75] Inventors: Edelbert Haefele, Karlsruhe; Michael Kotter, Bruchsal-Untergrombach, both of Fed. Rep. of Germany

[73] Assignee: Kernforschungszenthrum Karlsruhe GmbH, Karlsruhe, Fed. Rep. of Germany

[21] Appl. No.: 299,108

[22] Filed: Jan. 19, 1989

Related U.S. Application Data

[63] Continuation-in-part of Ser. No. 30,527, Mar. 27, 1987, abandoned.

[30] Foreign Application Priority Data

Mar. 27, 1986 [DE] Fed. Rep. of Germany ....... 3610363

[51] Int. Cl.$^5$ .......................... G01N 27/407
[52] U.S. Cl. .................... 204/153.14; 204/153.18; 204/153.19; 204/153.2; 204/406; 204/410; 204/412; 204/426
[58] Field of Search ............... 204/406, 1 F, 1 K, 1 N, 204/410, 412, 424, 425, 426, 427, 428, 429, 15; 364/497

[56] References Cited

U.S. PATENT DOCUMENTS

| | | | |
|---|---|---|---|
| Re. 28,792 | 4/1976 | Ruka et al. | 204/1 T |
| 3,620,931 | 11/1971 | Reichner | 204/1 T |
| 4,391,690 | 7/1983 | Lin et al. | 204/412 |
| 4,543,176 | 9/1985 | Harada et al. | 204/406 |

FOREIGN PATENT DOCUMENTS

| | | |
|---|---|---|
| 2918932 | 12/1983 | Fed. Rep. of Germany . |
| 3437452 | 4/1986 | Fed. Rep. of Germany ........ 422/94 |
| 205534 | 5/1982 | German Democratic Rep. ..................... 204/424 |
| 91358 | 5/1984 | Japan . |

OTHER PUBLICATIONS

James A. Plambeck, "Electroanalytical Chemistry", pp. 27-28 (1982).

*Primary Examiner*—G. L. Kaplan
*Attorney, Agent, or Firm*—Sughrue, Mion, Zinn, Macpeak & Seas

[57] ABSTRACT

A process and apparatus for continuously monitoring of concentrations of gaseous components in gas mixtures, with the exception of $O_2$. The desired concentration values are obtained simultaneously and separately for the individual gas components, without disruption and with relatively greater accuracy, by a direct path. The concentration of the gaseous component is continuously measured with the aid of at least one electrochemical cell having at least one solid body which contains oxygen-ion-conducting material and a metal-oxide-containing electrode, and generates electrical signals which are a function of the concentration of the component. The measurement signals are electronically and automatically evaluated in a computer which converts them into concentration values. The converted values are compared with reference values of a program which has been programmed into the computer earlier.

18 Claims, 13 Drawing Sheets

APPARATUS AND PROCESS FOR CONTINUOUSLY MONITORING CONCENTRATIONS OF GASEOUS COMPONENTS IN GAS MIXTURES, WITH EXCEPTION OF $O_2$

This is a continuation-in-part of Ser. No. 07/030,527 filed Mar. 27, 1987 and now abandoned.

BACKGROUND OF THE INVENTION

The present invention relates to a process and apparatus for continuously monitoring concentrations of gaseous components in gas mixtures, with the exception of $O_2$.

The measurement of oxygen as a component in a gas mixture with the aid of a solid body which contains a solid body electrolyte and platinum electrodes has long been known. In so doing, air is most often utilized as the reference gas. The upper surface of one side of the solid electrolyte is placed in contact with the gas mixture to be measured, and the upper surface of the other side of the solid electrolyte is placed in contact with air. The differential of the oxygen partial pressures then creates an electrical signal whose magnitude is dependent upon the concentration of oxygen in the measurement gas.

As proof of small concentrations of combustible gases, such as, for example, propane gas, sewer gas, hydrogen, or carbon monoxide in an air stream, a specially designed primary element was developed with an oxygen-ion-conducting dry electrolyte and two electrodes mounted on it, made up of metal layers, in which one electrode supports an overlay of an oxidizing catalyst. Such an apparatus is described in DE-PS No. 29 18 932. The oxidizing catalyst which is not in direct contact with the metal electrode, is described as containing at least one component of the group consisting of oxides of V, Cr, Mo, W, Fe, Ni, Co and Mn and the elements Pt, Ru, Rh and Pd. The electrodes can be covered by an electrically insulating layer of MgO and an activated carbon layer on top of that. Detection of the combustible gases occurs in such a manner that the combustible gas in the air stream which is to be detected is adsorbed equally or more strongly than the air-oxygen at the metal layers of the electrodes, and that the combustible gas is oxidized, with the oxygen contained in the air stream, at a temperature between about 250° C. and 450° C. on the spatially divided catalyst. In this process, therefore, all combustible gases present in the air stream are fully oxidized, the oxygen contained in the air stream reduced in its concentration, and the reference gas, which is required for reception of an electrical signal, created only after the oxidation reaction. The process that is deducible from DE-PS No. 29 18 932 thus allows only the detection of individual combustible gases in an air stream or, in the simultaneous presence of several combustible gases in the air stream, the determination of the sum of the concentrations of these combustible gases. Concentrations of noncombustible gaseous components in gas mixtures cannot be detected with the process and the measuring sensor from the above German patent publication. Nor is it possible to simultaneously and selectively detect different gaseous components (both combustible as well as noncombustible) with the process and the measuring sensor from the above German patent publication.

SUMMARY OF THE INVENTION

An object of the present invention therefore is to provide a process and an apparatus for continuously monitoring concentrations of gaseous components in gas mixtures, with the exception of $O_2$, for example, in exhaust gases from large furnaces, with which the desired concentration values simultaneously and separately for the individual gas components are received undisrupted and with relatively greater accuracy in a direct path. Another more limited object is to provide a process and apparatus for simultaneously monitoring several gas components.

Additional objects and advantages of the present invention will be set forth in part in the description which follows and in part will be obvious from the description or can be learned by practice of the invention. The objects and advantages are achieved by means of the processes, instrumentalities and combinations particularly pointed out in the appended claims.

To achieve the foregoing objects and in accordance with its purpose, the present invention provides a process for continuously monitoring the concentration of a gaseous component in a gas mixture, with the exception of $O_2$, comprising: (a) continuously generating and measuring electrical signals which are a function of the concentration of the gaseous component by bringing the gas mixture into contact with at least one electrochemical cell having at least one solid body which contains an oxygen-ion-conducting solid electrolyte material and a metal-oxide-containing electrode which generates electrical signals which are a function of the concentration of the component, and (b) automatically and electronically evaluating the measured signals in a computer which converts the measured signals into concentration values and compares the converted values with reference values of a program which was programmed into the computer earlier.

In another aspect of the present invention, there is provided a process for continuously monitoring and controlling the concentration of a gaseous component in a gas mixture in which at least one gaseous component is fed into the gas mixture, whereby a portion of the added gaseous component is used up in a reaction with at least one other gaseous component, comprising: (a) continuously generating and measuring electrical signals which are the function of the residual concentration of the component which is added or of the concentration of the component that is to be monitored by bringing the gas mixture into contact with at least one electrochemical cell having at least one solid body which contains an oxygen-ion-conducting solid electrolyte material and a metal-oxide-containing electrode and which generates, electrical signals which are a function of the residual concentration of the component which is added or of the concentration of the component which is to be monitored, (b) automatically and electronically evaluating the measured electrical signals in a computer which converts the measured signals into concentration values and compares the converted values with reference values of a program which was programmed into the computer earlier, and (c) automatically varying, by a signal from the computer, the amount of the component which is fed into the gas mixture in accordance with the level of differences between the converted values and the reference values of the program.

Preferably, the continuous measurement of the concentration of the gaseous component or the measurement of the residual concentration of the added component, in order to avoid the disruptive influences of the measurement signal with further gas components, is carried out by one of three techniques. In a first technique, the measurement is performed with the aid of an electrochemical cell which has no cross sensitivity with respect to the gas mixture components that are not measured.

In a second technique, the measurement is performed with the aid of at least two electrochemical cells, which are separated from one another and which are electrically cross-connected with one another. The electrochemical cells each have a measurement gas side. At least one of the electrochemical cells does not contain a catalyst on the measurement gas side and at least one of the electrochemical cells contains a catalyst on the measurement gas side for chemically converting at least one gas component. The gas component which is chemically converted can be converted by itself, (e.g. dissociation of NO to nitrogen and oxygen), that is, without reaction with any other gas component, or can be converted as the result of reaction with other gas components (e.g. oxidation of ammonia by oxygen).

In a third technique, the measurement is performed with the aid of an electrochemical cell which is in the form of at least two electrochemical partial cells, each of which have a measurement gas side, and at least one of which contains a catalyst on the measurement gas side for chemically converting at least one gas component. The gas component which is chemically converted can be converted by itself, that is, without reaction or can be converted as the result of reaction with any other gas component, with other gas components.

The measurement signal that is to be evaluated in the computer, which corresponds to the concentration of the component or to the residual concentration of the components which is to be monitored, is either a direct signal from a signal electrochemical cell (first technique) or is created by differential formation of the signal of the solid body without a catalyst which corresponds to the sum concentration of all gas components, to the signal of the solid body with a catalyst, which corresponds to the sum concentration of all gas components without the selectively chemically converted gas component (other techniques).

The present invention also provides an apparatus for carrying out the above process, which comprises a computer, with or without control elements, and a measurement unit which is comprised of one or more gas sampling probes made of a material that conducts oxygen ions and stays in contact with the measurement gas. The material that conducts oxygen ions has a measurement gas side which has a surface that faces the measurement gas and a reference gas side which has a surface that faces away from the measurement gas. An electrode is mounted on the surface of the material facing the measurement gas, and an electrode is mounted on the surface of the material faced away from the measurement gas. Electrical off-leads are provided for the signals that are generated. In the apparatus of the present invention, the electrode which is on the surface that faces the measurement gas is in the form a solid body structure. The solid body structure is comprised of (a) metallic components and oxidic components or (b) of oxidic components. One electrical off-lead is mounted on the surface which faces the measurement gas and one electrical off-lead is mounted on the surface which is turned away from the measurement gas.

The electrode can be present as either a porous solid body structure or it can be designed as an air-tight and, because of the required oxygen transport, sufficiently thin layer, for example, of only a few atom layers.

Known devices are used as computers and as control units.

In one preferred embodiment of the present invention, the apparatus comprises several sampling probes, and at least one of the probes has a gas-porous catalyst layer on the side which faces the measurement gas. The catalyst layer is positioned above the solid electrode structure and accelerates the chemical conversion of a gas component in the measurement gas. The catalyst layer closes off the interstitial space to the oxygen-ion-conducting material and to the solid electrode body structure.

In another embodiment of the apparatus according to the present invention, the probe has an element which divides the oxygen-ion-conducting material into at least two parts and which is made of a material that does not conduct oxygen ions. A catalyst layer which accelerates the chemical transformation of a gas component is positioned on the side which faces the measurement gas, and is positioned above at least one part of the material which is conducting a portion of the oxygen ions above the solid electrode body structure. The catalyst layer or layers are arranged, individually or all together, to close off the interstitial area to the oxygen-ion-conducting material and to the solid electrode body structure. Each part made of the oxygen-conducting material has a separate electrical off-lead.

Advantageously, the solid electrode body structure is made of an oxide or several oxides of at least one transition metal from the sub-groups IV, V, VIII and I of the periodic table of elements.

The solid electrode body structure can, however, also be made of one or more metals and of one or more oxides.

With the process according to the invention, for example, $NH_3$, CO, hydrocarbons, $NO_x$ and $SO_2$ as components of a mixture can be monitored, and adherence to desired concentration ranges controlled. As another example, the gas mixture can contain a chlorinated hydrocarbon, such as trichloroethane, as a component which is to be monitored and controlled to a desired concentration range.

With the process according to the invention, even small concentrations of ozone in a gas or gas mixture can be monitored.

The gas components that are to be studied can, depending on their type and the construction of the sampling probe, be measured to advantage in concentration ranges between 0 and as far as 2500 ppm.

BRIEF DESCRIPTION OF THE DRAWINGS

It is to be understood that both the foregoing general description and the following detailed description are exemplary and explanatory, but are not restrictive of the invention.

DETAILED DESCRIPTION OF THE INVENTION

Figure 1:
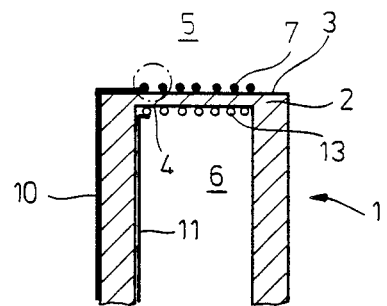
FIGS. 1 to 4 schematically show various examples of electrochemical cells that are made in accordance with the present invention. For each, only the probe heads or the parts of the electrochemical cells that are in contact with the gas mixture (measurement gas) are illustrated. Computers and control units, on the other hand, are not represented.

The advantages of the present invention in comparison to the known processes and apparatus, are to be seen in the fact that the concentrations of gaseous components of gas mixtures, according to the case in which it is applied, can be measured over a broad range of concentration. The characteristics of the apparatus according to the present invention are adjustable through appropriate choices of the type of electrodes and of the operational temperature. In the use of oxides and mixed oxides, there result very many possible choices for the composition of the electrode. From this great diversity, a specific electrode can be developed for each gaseous component of a gas mixture or for each supplemental gaseous component which is added to a gas mixture. In so doing, it makes no difference whether only one component or several are to be detected at the same time by use of several electrochem. cells, respectively at least one for each component (see FIG. 22). Moreover, a continuous monitoring of the concentration, which monitoring is undisturbed by other gas components, is possible for each individual component. This method of operation cannot be carried out with the measuring sensor according to DE-PS No. 29 18 932, and not at all when there are several combustible gases in the air stream whose concentrations change in various ways over the course of time. The known measuring sensor can produce useful measurement values only when there is only one single combustible gas present in the air stream, or when only the summation value of all combustible gases is of interest.

While with the present invention measurements are made using the surrounding air as the reference gas, the known measuring sensor operates with the measurement gas, liberated from the combustible gas, serving as its reference gas. Such a method of operation is not necessary with the apparatus according to the present invention. With the present invention, the simultaneous monitoring of several gas components is made possible by the fact that, for the electrodes of the measurement gas side, different compositions are used for different gas components.

What is measured each time is the oxygen activity, which depends upon the local composition of the boundary surface of the oxide electrode which is influenced by the measurement gas.

In comparison to the results that can be obtained with the measurement sensor according to DE-PS No. 29 18 923, the results obtained with the apparatus according to the present invention prove that the apparatus according to the present invention demonstrates a significantly greater sensitivity, and indeed, at least by a factor greater than or equal to 10 (greater than 15 for CO). The operational temperature of the sampling probes according to the present invention can, according to the gas component to be measured and according to the oxide electrode to be employed, be selected in a relatively broad range. It turned out that at relatively high temperatures, such as 550° C. for example, very small time constants are attained, e.g. a time constant $\tau$ (50% final value) clearly under a second.

As oxide-containing electrodes which are in contact with the measurement gas and generate useful electrical signals in interaction with the reference electrode, those made of $Co_3O_4$ can be used for the measurement of $C_4H_{10}$ or $SO_2$ sensitivity in the presence of $NH_3$, CO or NO. For the measurement of $NH_3$, an electrode made of $V_2O_5$ can be used without transverse sensitivity in the presence of CO or $C_4H_{10}$. For the measurement of CO or $NH_3$, an electrode made of Pt.CuO can be used without transverse sensitivity in the presence of $CH_4$. With electrodes which contain either $Co_3O_4$ or $TiO_2$, ozone can be measured in an air stream, but not with an electrode which contains $V_2O_5$.

Table 1 shows an exemplary comparison of the suitability of each of the electrodes for the detection of the gas components considered (valuation: +++, ++, +, o, where o represents no suitability for detecting the gaseous components and +++ represents the highest suitability for detecting the gaseous components).

TABLE 1

| Component | Electrode | | | | | |
|---|---|---|---|---|---|---|
| | $Pt.V_2O_5$ | $V_2O_5$ | Pt.CuO | $TiO_2$ | $Pt.Co_3O_4$ | $Co_3O_4$ |
| CO | +++ | o | ++ | + | o | o |
| $NH_3$ | +++ | ++ | ++ | + | + | o |
| $SO_2$ | | + | | ++ | | ++ |
| $CH_4$ | | | o | | o | |
| $C_4H_{10}$ | | o | | ++ | o | +++ |
| NO | | + | + | o | o | o |
| $O_3$ | | o | | ++ | | +++ |

If, as a component of a gas mixture, $NO_x$ is supposed to be monitored or controlled in its concentration, $NH_3$ can be employed as a supplemental component fed into the gas mixture for the purpose of reducing the $NO_x$. Correspondingly, with an NO content in the gas mixture, CO can be applied as a reducing supplemental component. By measuring the residual concentration of $NH_3$, with knowledge of the input amount, the concentration of the $NO_x$ in the gas mixture can be measured, monitored and controlled. The measurement of the $NO_x$ or NO content can, however, take place in a direct way with a sampling probe which, for example, contains $V_2O_5$.

In the case of using an electrode made of $Pt.V_2O_5$ for measuring $NH_3$ in the simultaneous presence of CO, $NH_3$ can be selectively detected combined with a catalyst layer which contains $V_2O_5.TiO_2$ as an effective component on an underlayer of $Al_2O_3MgO.SiO_2$ as an effective component on an underlayer of $Al_2O_3.MgO.SiO_2$. (see FIG. 3, right part)

The invention is described—as follows—with the aid of some illustrations and a few exemplary attempts to measure gaseous components in gas mixtures.

Referring now to the drawings, there is shown in FIG. 1 the head of a single sampling probe 1 in the form of a tube closed on one end and made from a solid electrolyte 2, such as, for example, zircon-stabilized yttrium oxide. The closed end of the tube has an inner side 4 which faces a reference gas 6 and an outer surface 3 which faces the gas to be measured (measurement gas). An electrode 13 made of platinum, for example, is mounted on the inner side 4, which faces the reference gas 6, such as, for example, air. A sampling electrode in the form of a porous solid body structure 7 is mounted on the surface 3 of the solid electrolyte 2 (and/or of the oxygen-ion-conducting material) which faces the measurement gas. Electrode 7 can be made of either one or more oxides, or of one or more metallic components and one or more oxidic components. An electrical off-lead 10 is mounted on the surface 3 of the solid electrolyte 2 which faces the measurement gas 5 and an electrical off-lead 11 is mounted on the surface 4 which faces the reference gas 6. The electrical off-leads 10 and 11 can, for example, be made of lead channels made of gold.

Figure 2:
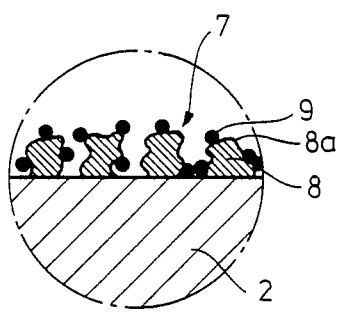

FIG. 2 shows a section from the area of the surface 3 which faces the measurement gas 5, and shows a part of the porous solid body structure 7 which is mounted on it. FIG. 2 has as its basis a version of the solid body structure 7 which has two metallic components 8 and 8a and an oxidic component 9. In the current example, metallic component 8 is made of platinum, and metallic component 8a, which has been mounted supplementally and which at least partially covers the platinum surface, is made of rhodium. The oxidic component 9 can, for example, be made of $V_2O_5$. While the thickness of the solid electrolyte layer 2 can amount to about 1 mm between the two electrodes, the solid body structure 7 has a thickness of about 5 μm altogether.

Figure 3:
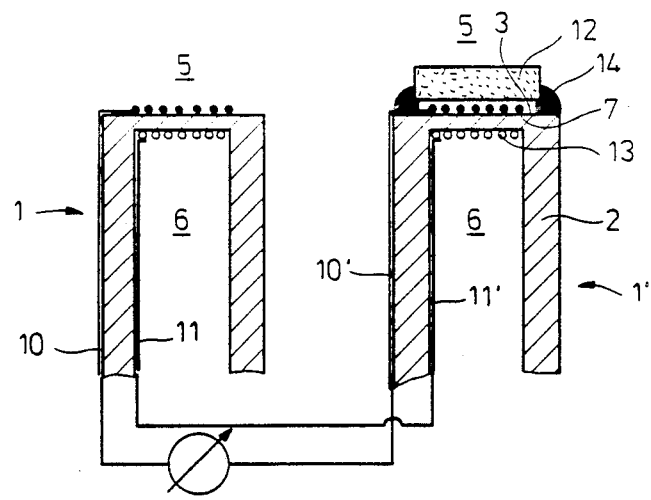

FIG. 3 shows two sampling probe heads 1 and 1' separated spatially from one another, with probe head 1 having electrical off-leads 10 and 11, and probe head 1' having electrical off-leads 10' and 11'. Here, probe head 1 is designed in the way already described above in connection with FIGS. 1 and 2, and the other probe head 1' is similarly designed but has a gas-permeable catalyst layer 12 above the porous solid body structure 7. Catalyst layer 12 seals off the interstitial space, so that it is airtight, to the oxygen-ion-conducting material 2 and to the solid body structure 7. Catalyst layer 12 can be shaped like a tablet and affixed with a ceramic adhesive 14 onto the surface 3 of the solid electrolyte that faces the measurement gas 5. If the catalyst tablet is made up of a material which accelerates the reaction

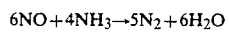

$$6NO + 4NH_3 \rightarrow 5N_2 + 6H_2O$$

then, in the simultaneous presence of NO and $NH_3$ in the measurement gas 5 at sampling probe 1, the actual concentration of $NH_3$ in the gas vis-a-vis the $NH_3$ concentration of approximately 0 is measured at sampling probe 1'. The difference signal is only a measure of the ammonia concentration in 5.

Figure 4:
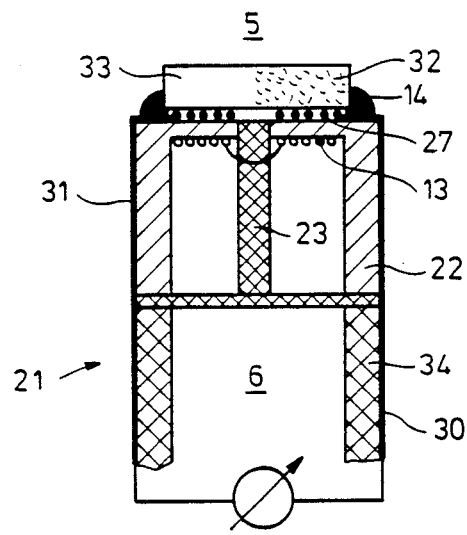

FIG. 4 shows a different version of the apparatus according to the present invention in which two solid body networks are united in a sampling probe 21 and are separated by an element 23 made of an inert material. Both of the solid body networks of this probe 21 are mounted on a tube 34 made of an insulating oxide ceramic. Set above the solid body structure 27 of the two half cells is a porous tablet 32-33. One half 32 of the tablet is made of a catalyst layer, and the other half 33 is made of inert material. The electrical signal can be detected by way of an off-lead 30 on the side of the catalyst layer and an off-lead 31 on the side of the inert material.

Figure 21:
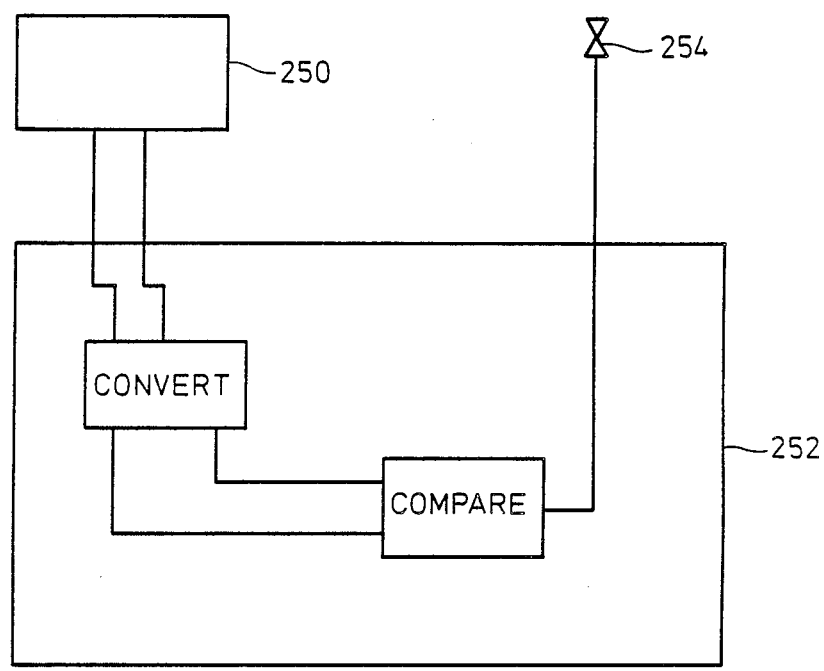
FIG. 21 schematically shows in block diagram form an electrochemical cell and computer in accordance with the present invention.

FIG. 21 shows an electrochemical cell 250 which is connected to a computer 252. Computer 252 evaluates the measured signals from cell 250 and converts them into concentration values. The computer then compares the concentrations values with reference values. The computer can then send a signal to a valve 254 which controls the amount of additional gas which is added to a gas mixture.

Figure 22:
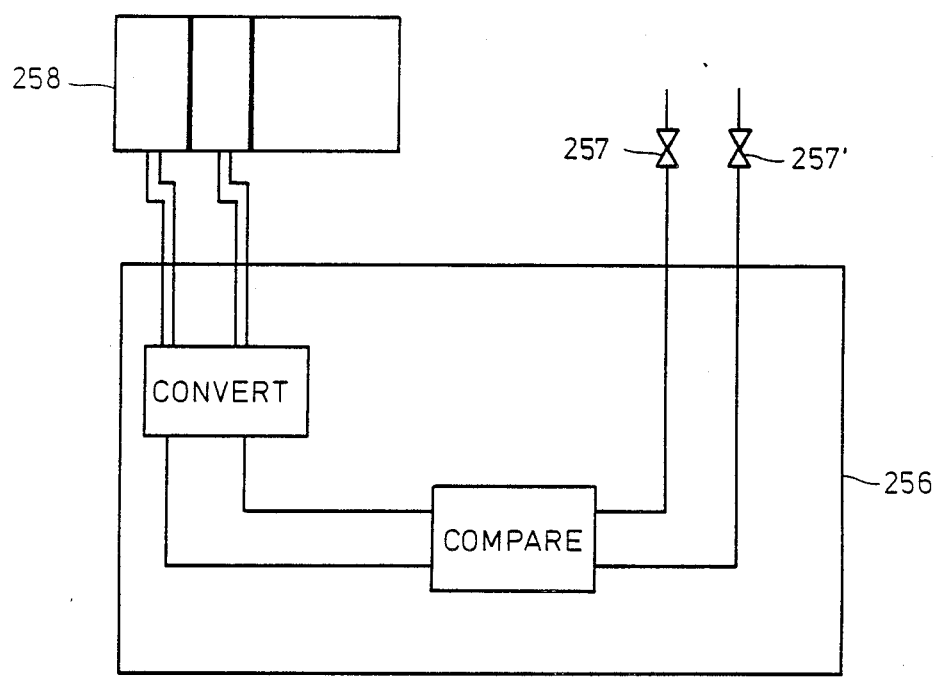
FIG. 22 shows a similar system with several electrochemical cells.

A similar configuration is shown in FIG. 22 where a sensor system 255 with several electrochemical cells measures the concentrations of several components in the gas mixture. The computer 256 sends signals to the valves 257, 257' etc.

By means of the present invention, the qualitative composition of an unknown gas mixture is not to be determined. It is much rather the time-related changes in the concentrations of certain components in a gas mixture which are to be monitored. For this purpose it is necessary that (a) the partial oxygen pressure is known and preferably remains constant and (b) the qualitative composition of the gas mixture is known.

Thus, the present invention relates to monitoring and/or controlling the concentration of a particular gaseous component.

Such measuring problems often appear in technology, for example, in the operation of a combustion installation.

Here, generally the material to be burned (the fuel) remains largely constant in its composition. If the combustion conditions are also constant, the waste gas will also remain constant in its composition over time.

Legislatures often set maximum values for the emission of certain components of waste gases. Consequently, the concentration of these waste gases. Consequently, the concentration of these components has to be continuously monitored, as in principle a change in the composition of the fuel and/or combustion conditions cannot be ruled out.

A number of procedures for the determination of the partial oxygen pressure of a gas mixture are known in the prior art. The determination of the partial oxygen pressure thus is part of the state of the prior art and such prior art techniques can be used in the present invention.

In addition, the electro-chemical cell employed in the present invention reacts considerably more sensitively to changes in the concentration of the gases which are to be monitored by the present invention than to the changes in the partial oxygen pressure. This is shown below on the basis of the Nernst equation for ammonia ($NH_3$).

The Nernst equation is $$E = 2.3(RT/4F) \log (P_{O_2}/P^*_{O_2})$$

Legend:
E: Potential
R: Gas constant
T: Temperature in Kelvin
F: Amount of electricity (1 Faraday = 1 F = 96494 Coulomb)
$P_{O_2}$: Partial pressure of oxygen in the measuring gas
$P^*_{O_2}$: Partial pressure of oxygen in air ($P^*_{O_2} = 0.21$ bar).
log: Decimal logarithm With a measuring temperature of 450° C., the expression 2.3 (RT/4F) assumes the value of 35.8 mV.

If the partial pressure of oxygen varies, for example, between 4 and 8%, E changes by 11 mV.

The analogous calculation for ammonia results in the fact that the potential changes by 16 mV if the concentration of ammonia is raised from 4 to 8 ppm.

The electrolytic cell thus reacts considerably more sensitively to variations of ammonia (and the other gases) than to the variations of the oxygen concentration.

In the combustion process referred to above (and in similar processes) it is thus often quite sufficient to measure the oxygen concentration once during stationary operation and, assuming that this concentration is constant, to monitor the concentration of the remaining gas components.

For this reason a constant oxygen concentration of 3 percent by volume was used in each of the following examples of the present application.

EXAMPLE 1

An additive gas was added to a starting gas mixture comprised of nitrogen plus 3 percent-by-volume oxygen. In five separate experiments, a different additive gas was added singly (without addition of any other additive gas) to the starting gas mixture. In each experiment, varying amounts of additive gas were added to the starting gas mixture to produce a number of final gas mixtures which had different concentrations of the added gas. The nature of the added gas for each experiment and the concentrations in which it was employed are shown in Table 2 below.

TABLE 2

| Exp. No. | Added Gas | Concentrations of Added Gas |
| --- | --- | --- |
| 1 | $C_4H_{10}$ | 10, 20, 50 and 100 ppm |
| 2 | $SO_2$ | 50, 100 and 200 ppm |
| 3 | $NH_3$ | 10, 20, 50, 100 and 200 ppm |
| 4 | CO | 10, 20, 50, 100 and 200 ppm |
| 5 | NO | 50, 100 and 200 ppm |

Figure 5:
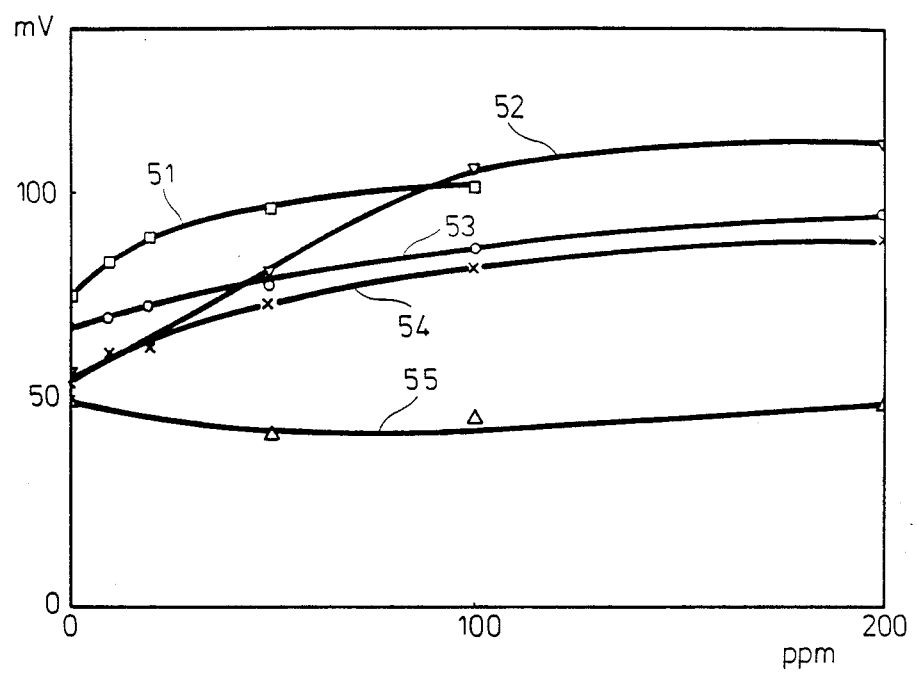
FIGS. 5 to 20 and 23 show test results for tests that were conducted to illustrate the operation of the method and apparatus of the present invention.

All gas mixtures were studied, with regard to the components added, with a sampling probe which contained an oxide electrode made of $TiO_2$. The operational temperature during the measurement was 450° C. For each experiment, the probe signals, received in mV, are shown in FIG. 5 as a function of the concentrations of the added component. Curve 51 represents the values for $C_4H_{10}$, Curve 52 for $SO_2$, Curve 53 for $NH_3$, Curve 54 for CO and Curve 55 for NO.

EXAMPLE 2

Figure 6:
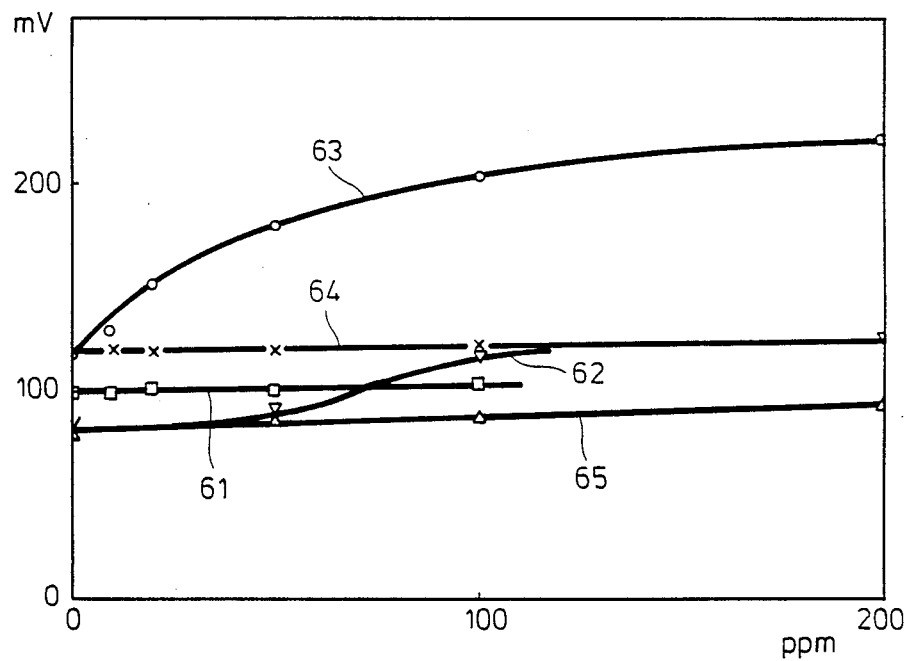

The same starting gas mixture, as described in Example 1, with the same concentrations of the named additive gases, was measured at the same operational temperature with a sampling probe which contained $V_2O_5$ as the oxide electrode. The probe signals, received in mV, are shown in FIG. 6 as a function of the concentrations of the added components. Curve 63 shows the values for $NH_3$, Curve 64 for CO, Curve 61 for $C_4H_{10}$, Curve 62 for $SO_2$ and Curve 65 for NO.

EXAMPLE 3

Figure 7:
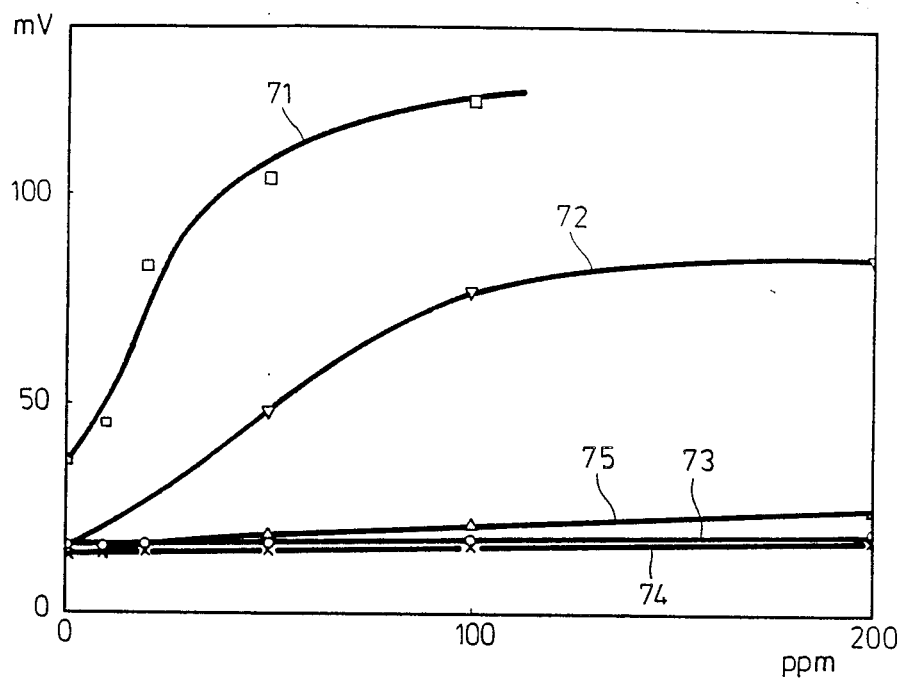

Corresponding measurements were carried out with the same gas mixtures in the same conditions as in Example 1, except that a sampling probe was used which contained $Co_3O_4$ as an oxide electrode. The received probe signals, measured in mV, are shown in FIG. 7 as a function of the concentrations of the added components. Curve 71 shows the values for $C_4H_{10}$, Curve 72 for $SO_2$, Curve 75 for NO, Curve 73 for $NH_3$ and Curve 74 for CO.

EXAMPLE 4

In four separate experiments, a different additive gas was added singly to a starting gas mixture comprised of nitrogen and 3 percent-by-volume oxygen. In each experiment, varying amounts of additive gas were added to the starting gas mixture to produce a number of final gas mixtures which had different concentrations of the added gas. The nature of the added gas and the concentrations in which it was employed are shown in Table 3 below.

TABLE 3

| Exp. No. | Added Gas | Concentrations of Added Gas |
| --- | --- | --- |
| 6 | $CH_4$ | 50, 100, 200 and 500 ppm |
| 7 | $NH_3$ | 10, 20, 50, 100, 200 and 500 ppm |
| 8 | CO | 10, 20, 50, 100 and 200 ppm |
| 9 | NO | 50, 100, 250 and 500 ppm |

Figure 8:
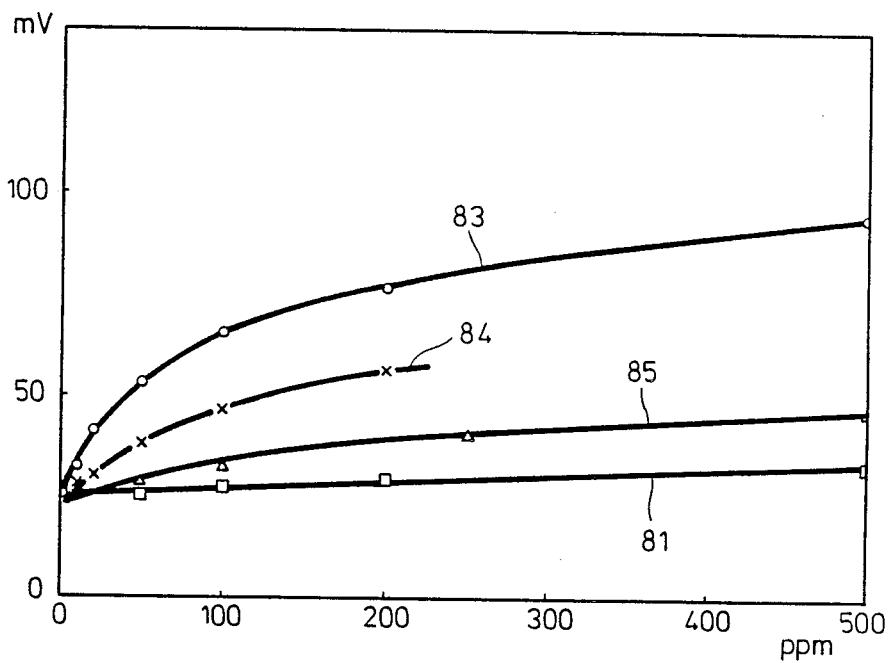

The gas mixtures were examined at a temperature of 450° C. with a sampling probe which contained an oxide electrode made of $Pt.C\mu O$. For each experiment, the probe signals, received in mV, are shown in FIG. 8 as a function of the concentrations of the added components. Curve 81 represents the values for $CH_4$, Curve 83 for $NH_3$, Curve 84 for CO and Curve 85 for NO.

EXAMPLE 5

Figure 9:
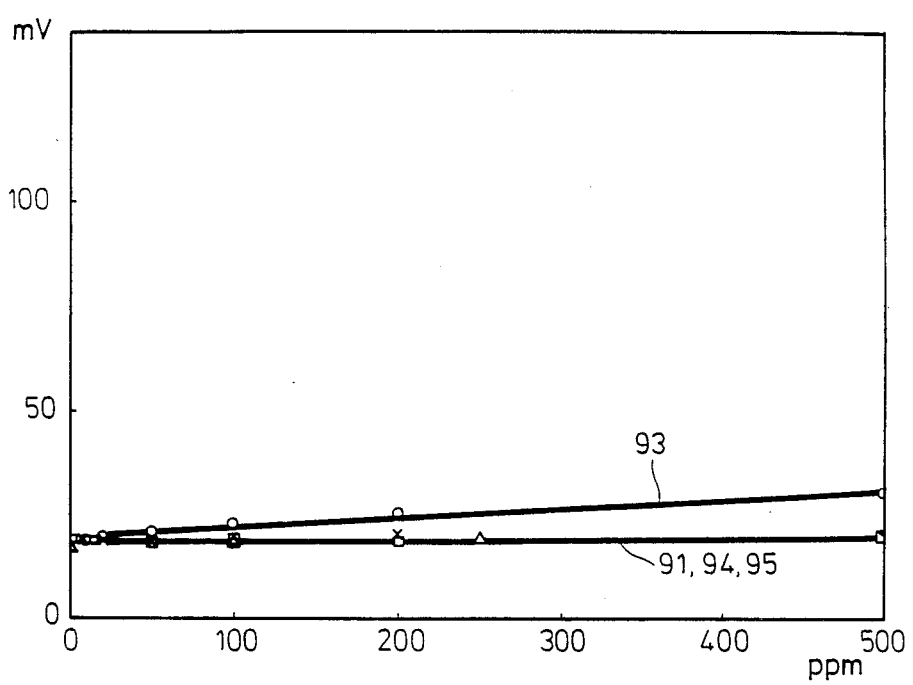

Under the same operational conditions described in Example 4, the identical gas mixtures were studied with the aid of a sampling probe having an oxide electrode made of $Pt.Co_3O_4$. The probe signals are shown in FIG. 9, with Curve 93 showing the values for $NH_3$. The corresponding signals for the final gas mixtures containing CO, $CH_4$ and NO are shown in Curve 91/94/95 of FIG. 9.

EXAMPLE 6

A carrier gas comprised of nitrogen and 3 percent-by-volume oxygen had added to it either $NH_3$ at different concentrations or CO at different concentrations. The concentrations in the resulting final gas mixtures are shown in Table 4 below.

TABLE 4

| Exp. No | Added Gas | Concentrations of Added Gas |
| --- | --- | --- |
| 10 | $NH_3$ | 10, 20, 50, 100, 300 and 500 ppm |
| 11 | CO | 100, 200, 300 and 500 ppm |

Figure 10:
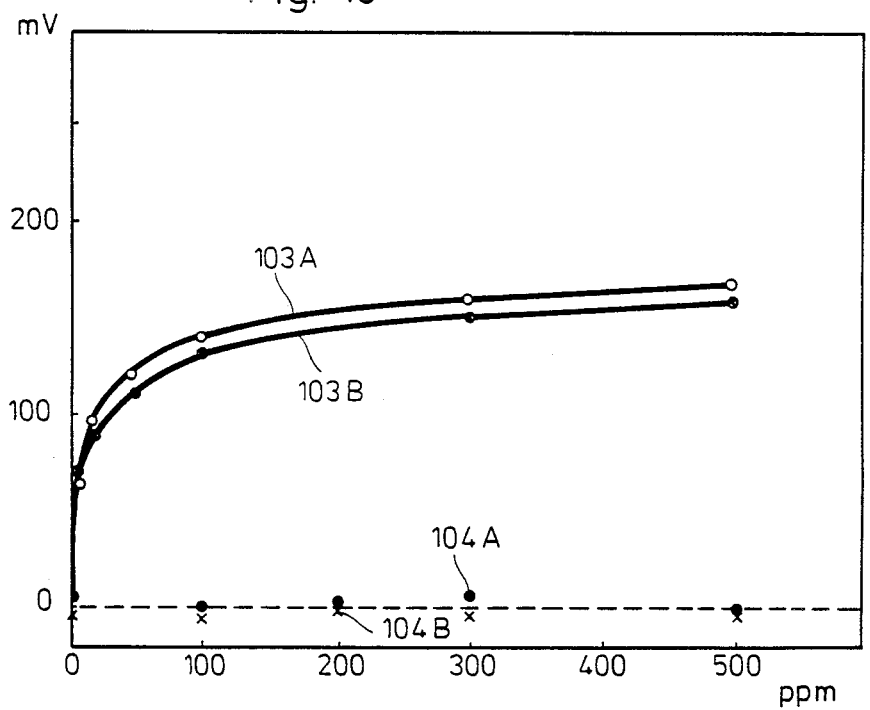

Each of the gas mixtures were subjected to measurement at 450° C. with an apparatus made of two separated probes, referred to here as apparatus A and constructed in accordance with the apparatus of FIG. 3, and also with an apparatus having a probe made of two half-cells, referred to here as apparatus B and constructed in accordance with the apparatus of FIG. 4. The probe signals, ascertained in mV, are shown in FIG. 10 as a function of the concentration of the added gas. With the probes that were used, signals for monitoring were not received for CO with either the apparatus comprised of the two separated probes (Apparatus A) as shown in Curve 104A of FIG. 10, or with the apparatus comprised of the probe with two half-cells (Apparatus B) as shown in Curve 104B in FIG. 10.

In contrast to this, when $NH_3$ was measured with these apparatus, the resulting curves lay next to one another and each showed a steep rise, particularly for concentrations in the range of 0 to 50 ppm, as can be seen by Curve 103A for the apparatus with two separated probes and Curve 103B for the apparatus having a probe made of two half-cells. In all the observed cases, the electrode material was made of $Pt.V_2O_5$. The catalyst, connected in a series, of the second probe 1' of Apparatus A or of the second half-cell of the probe 21 of Apparatus B (see FIGS. 3 and 4) comprised $V_2O_5$.-$TiO_2$ on $Al_2O_3.MgO.SiO_2$.

EXAMPLE 7

Figure 11:
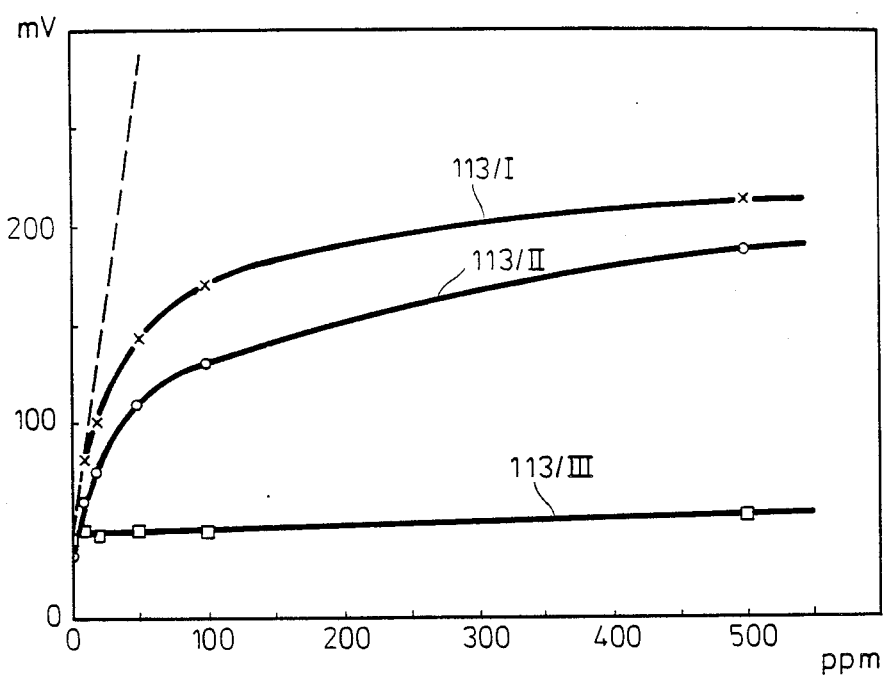

Gas mixtures formed by adding $NH_3$ in concentrations of 10, 20, 50, 100 and 500 ppm to a carrier gas of nitrogen with 3 percent-by-volume oxygen were subjected to measurement at 550° C. using different porous solid body structures as electrodes on the measurement gas side. FIG. 11 shows the results. Curve 113/I was obtained with an electrode made of $Pt.V_2O_5$. Curve 113/II was obtained with an electrode made of $Pt.Rh.V_2O_5$. For the sake of comparison, the different $NH_3$ concentrations also were measured with an electrode made of pure platinum (without oxide) as a porous solid body structure. Curve 113/III for the pure platinum electrode shows practically no rise in the probe signals, and is consequently of no use for monitoring $NH_3$ in a gas mixture. The dashed line shows, as a tangent of the first part of Curve 113/I, the rise of this curve in the range of 0 to 10 ppm of $NH_3$, and demonstrates the quality of the $Pt.V_2O_5$ electrode in that there is a rise of 4 mV/ppm of $NH_3$.

EXAMPLE 8

The procedure of Example 7 was repeated with the same gas mixtures, using the same electrodes, except that the probe signals alone were measured at a lower temperature, namely at 450° C. The corresponding curves are shown in FIG. 12, where Curve 123/I shows the values for the $Pt.V_2O_5$ electrode, Curve 123/II for the $Pt.Rh.V_2O_5$ electrode, and Curve 123/III for the Pt electrode on the measurement side.

Figure 12:
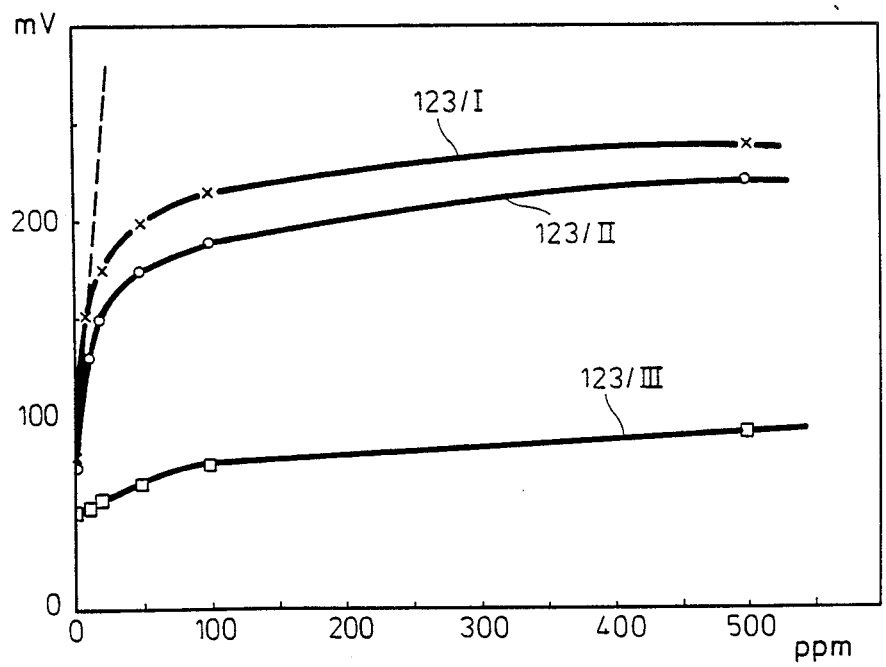

The curves in FIG. 12 produce a similar picture as in FIG. 11 in Example 7, with the modification that in FIG. 12 curves with higher signal values in mV have been the result. The dashed line in FIG. 12 shows the rise of Curve 123/I in the range of 0 to 10 ppm of $NH_3$, which takes an even steeper course (a rise of 7 mV/ppm of $NH_3$) than the corresponding portion of Curve 113/I in FIG. 11.

EXAMPLE 9

Figure 13:
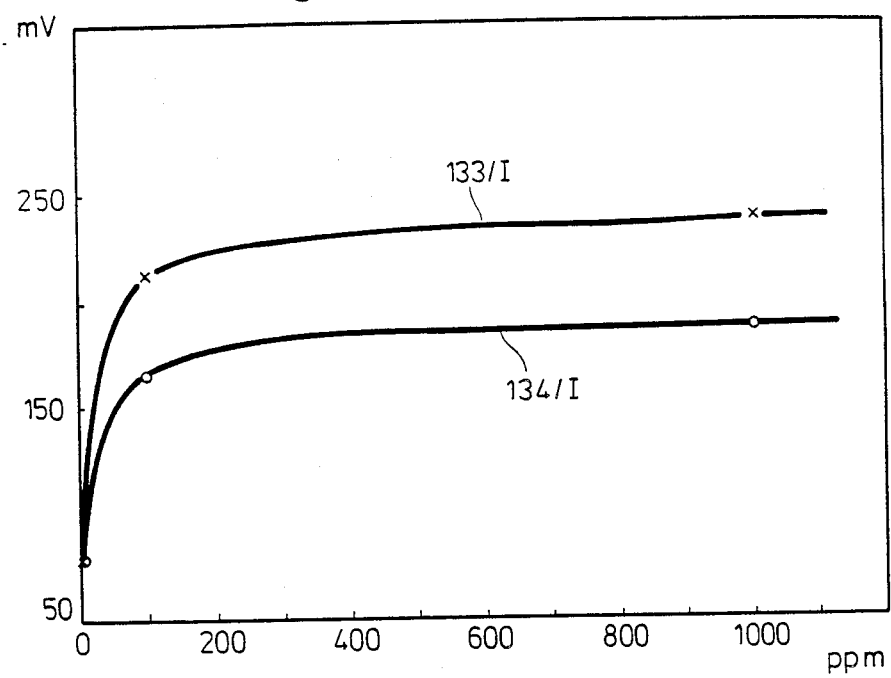

In a first experiment, measurement gases were produced by the addition of 100 ppm and 1000 ppm of $NH_3$ to a starting gas mixture comprised of nitrogen with 3 percent-by-volume oxygen. In a second experiment, measurement gases were produced by the addition of 100 and 1000 ppm of CO to the same starting mixture comprised of nitrogen and 3 percent-by-volume oxygen. The measurement gases were measured and the resulting probe signals in mV were detected using an oxide electrode of $Pt.V_2O_5$ at 450° C. A comparison of the results, which are represented in FIG. 13, shows that at first both the $NH_3$ Curve 133/I as well as the CO Curve 134/I have slopes of unequal steepness, each up to 100 ppm, but thereafter they rapidly flatten out. The values for the probe signals for $NH_3$ concentrations are higher than those for CO concentrations.

EXAMPLE 10

Figure 14:
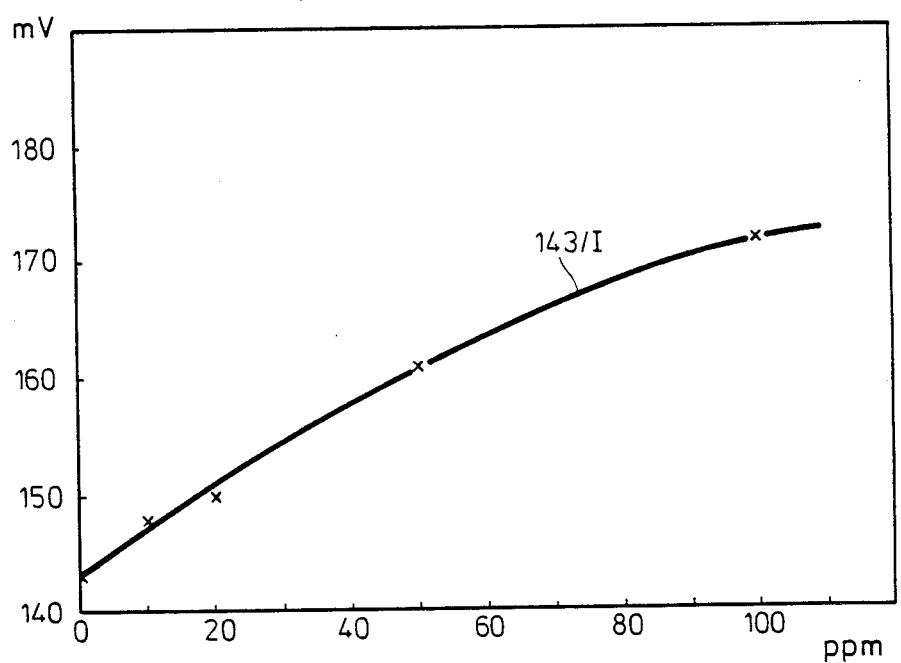

To a gas mixture comprised of nitrogen, 3 percent-by-volume oxygen, 200 ppm of NO and 200 ppm of CO were added 10, 20, 50 and 100 ppm of $NH_3$. A sampling probe having an oxide electrode made of $Pt.V_2O_5$ was used to measure probe signals in mV at 450° C. for the $NH_3$ component. As shown in Curve 143/I in FIG. 14, the values for the probe signals lay in fact somewhat lower than comparable experiments in a gas mixture of nitrogen and only 3 percent-by-volume oxygen, but Curve 143/I does show a well-utilizable course for monitoring smaller concentrations of $NH_3$ in such a gas mixture.

EXAMPLE 11

In this example, $NH_3$ inputs of 100 ppm and 1000 ppm were added into a gas mixture of nitrogen and 3 percent-by-volume oxygen, and in three separate experiments the probe signals in mV were measured. Each experiment employed a different oxide electrode and in each experiment a number of temperatures between 350° C. and 650° C. were employed. The three different oxide electrodes and the Figures which show the results for these electrodes are shown below of:

| Exp. No. | Electrode Material | FIG. NO. |
|---|---|---|
| a | $Pt.TiO_2$ | FIG. 15 |
| b | $Pt.V_2O_5$ | FIG. 16 |
| c | $Pt.TiO_2.V_2O_5$ | FIG. 17 |

Figure 15:
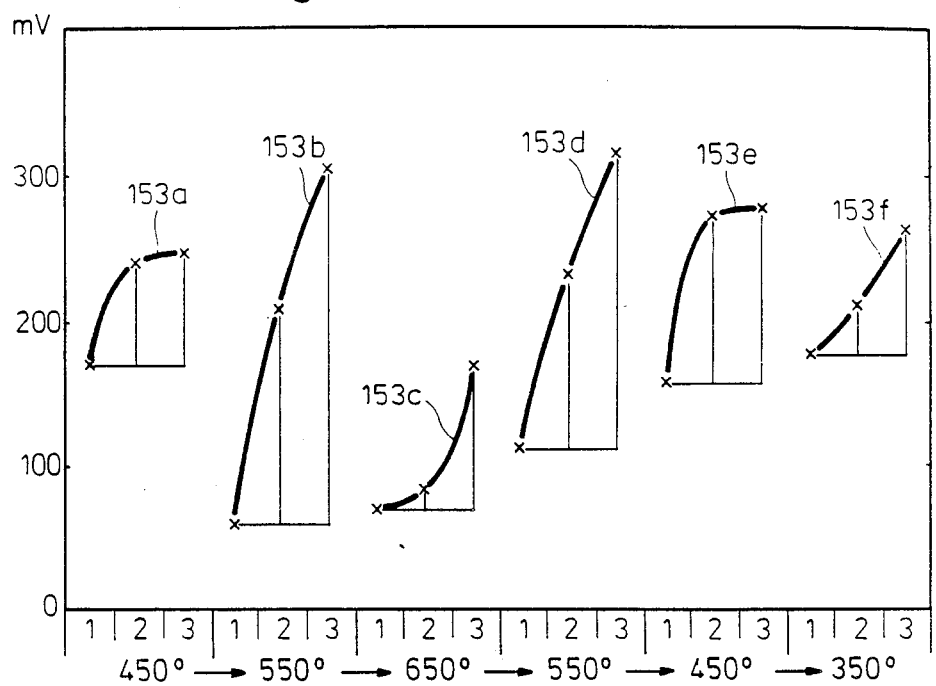
Figure 16:
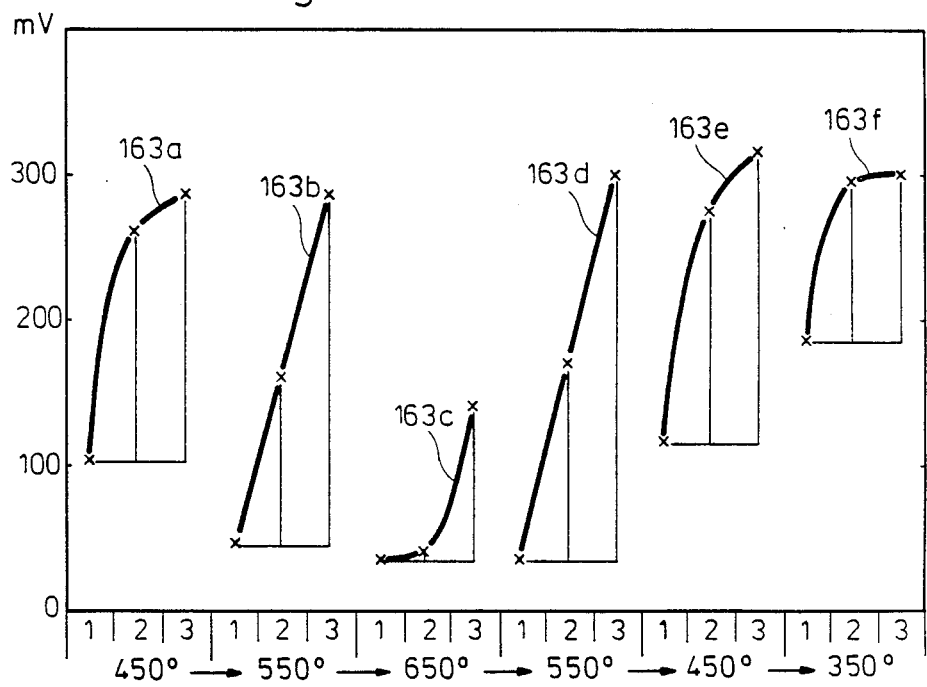
Figure 17:
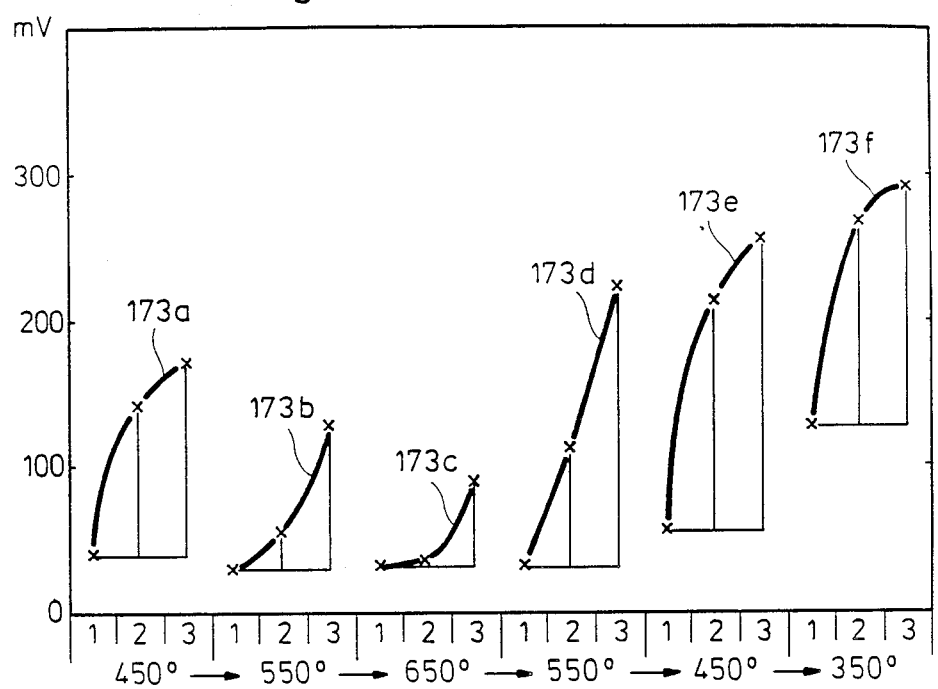

For all three experiments (a, b and c), the probe signals in mV were measured under comparable conditions. i.e. on one hand for the gas mixture without any added $NH_3$ (1), gas mixture plus 100 ppm of $NH_3$ (2), gas mixture plus 1000 ppm $NH_3$ (3) and, on the other, at temperatures which, beginning at 450° C., were at first raised step-by-step by 100° C. and then once again were lowered by the same difference to 350° C. As the sampling probes were prepared at a relatively low temperature of 450° C. before running through the temperature cycle, one may expect, as FIGS. 15 through 17 show, that the high-temperature treatment has an influence on the characteristic property of the sampling probe. Above all, these measurements show that, depending upon the temperature, $NH_3$ can be measured in different concentration ranges.

EXAMPLE 12

Figure 18:
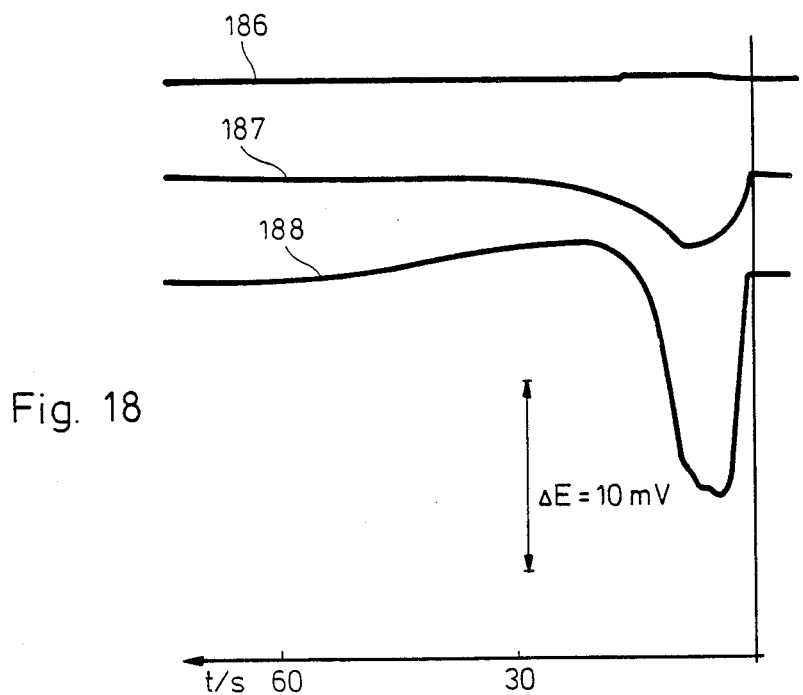
Figure 19:
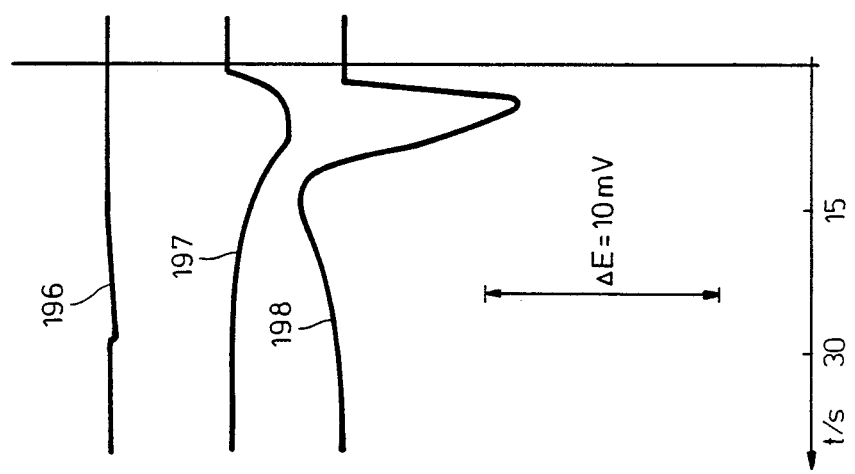

In a first experiment at 400° C., the results of which are shown in FIG. 18, and in a second experiment at 450° C., the results of which are shown in FIG. 19, the effect of ozone in an oxygen stream was examined on three different oxide electrodes. Here, the brief and one-time addition of ozone (V=5 ml, conc. $O_3$=20 $\mu g/l$) to the oxygen stream ($\dot{v}$=10 ml/sec) using $Co_3O_4$ as an electrode produced a well-formed peak, both in the first experiment as shown in Curve 188 in FIG. 18, and in the second experiment as shown in Curve 198 in FIG. 19.

A less well-formed peak was observed with $TiO_2$ as the electrode, both in the first experiment as shown in Curve 187 in FIG. 18, and in the second experiment as shown in Curve 197 in FIG. 19.

With $V_2O_5$ as the electrode, there was no sensitivity with respect to ozone, both in the first experiment as shown in Curve 186 in FIG. 18, and in the second experiment as shown in Curve 196 in FIG. 19.

EXAMPLE 13

Figure 20:
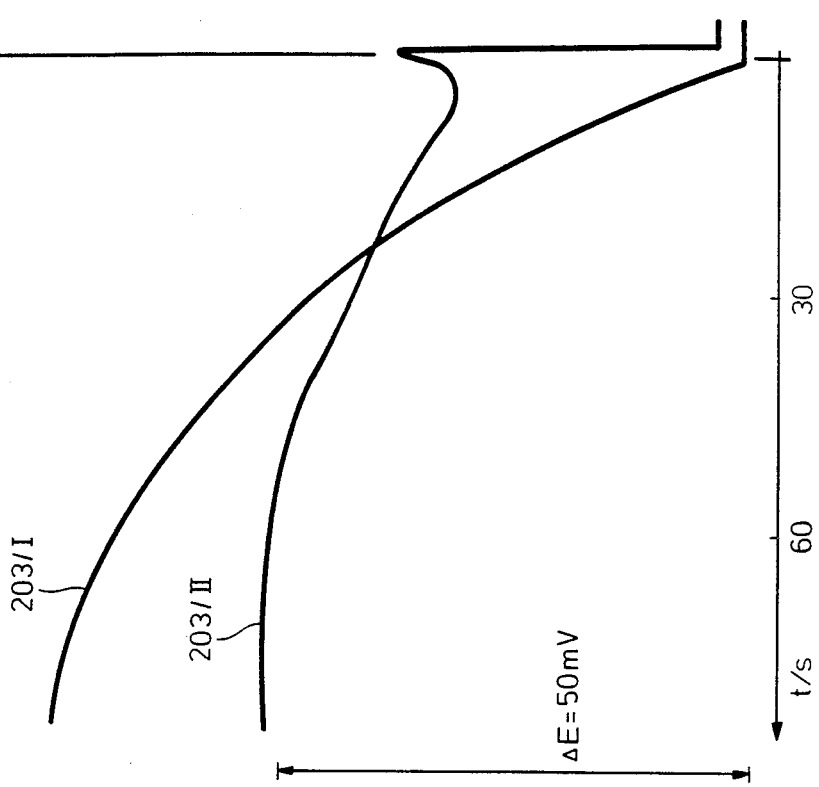

In this example, during a uniform admixture from the starting point on of 20 ppm of $NH_3$ into a gas mixture of nitrogen and 3 percent-by-volume oxygen, the speed of response was examined when there was a temperature of 550° C. and two different oxide electrodes. The results are shown in FIG. 20.

Curve 203/I shows the values for Pt.$V_2O_5$ as the oxide electrode, and Curve 203/II shows the values for an electrode Pt.Rh.$V_2O_5$. It can be recognized from Curve 203/II that within a time span of less than 1 second, 50% of the final signal values were received.

A summarizing representation of the measurements which were conducted is provided in the following Tables 5a and 5b.

TABLE 5a

Carrier Gas Measurement Side: 3% $O_2$ in $N_2$
Reference Gas: Surrounding Air

| Electrode Material | Temp. (Celsius) | Gas Component or Residual Concentration of Input Component in Carrier Gas of the Measurement Side to be Measured | Representation in FIG. NO. | Curve No. |
|---|---|---|---|---|
| Pt | 450 | 0–500 ppm $NH_3$ | 12 | 123/III |
| Pt | 550 | 0–500 ppm $NH_3$ | 11 | 113/III |
| Pt.$V_2O_5$ | 450 | 0–500 ppm $NH_3$ | 12 | 123/I |
| Pt.$V_2O_5$ | 450 | 0–1000 ppm $NH_3$ | 13 | 133/I |
| Pt.$V_2O_5$ | 450 | 0–1000 ppm CO | 13 | 134/I |
| Pt.$V_2O_5$ | 550 | 0–500 ppm $NH_3$ | 11 | 113/I |
| Pt.Rh.$V_2O_5$ | 450 | 0–500 ppm $NH_3$ | 12 | 123/II |
| Pt.Rh.$V_2O_5$ | 550 | 0–500 ppm $NH_3$ | 11 | 113/II |
| Pt.$TiO_2$ | 350–650 | 0–1000 ppm $NH_3$ | 15 | 153 a-f |
| Pt.$V_2O_5$ | 350–650 | 0–1000 ppm $NH_3$ | 16 | 163 a-f |
| Pt.$TiO_2$.$V_2O_5$ | 350–650 | 0–1000 ppm $NH_3$ | 17 | 173 a-f |
| Pt.CuO | 450 | 0–500 ppm $NH_3$ | 8 | 83 |
| Pt.CuO | 450 | 0–200 ppm CO | 8 | 84 |
| Pt.CuO | 450 | 0–1000 ppm $CH_4$ | 8 | 81 (to 500 ppm) |
| Pt.CuO | 450 | 0–2500 ppm NO | 8 | 85 (to 500 ppm) |
| Pt.$Co_3O_4$ | 450 | 0–500 ppm $NH_3$ | 9 | 93 |
| Pt.$Co_3O_4$ | 450 | 0–200 ppm CO | 9 | 94 |
| Pt.$Co_3O_4$ | 450 | 0–1000 ppm $CH_4$ | 9 | 91 |
| Pt.$Co_3O_4$ | 450 | 0–1000 ppm $CH_4$ | 9 | 91 (to 500 ppm) |
| Pt.$Co_3O_4$ | 450 | 0–2500 ppm NO | 9 | 95 (to 500 ppm) |
| $Co_3O_4$ | 450 | 0–500 ppm $NH_3$ | 7 | 73 (to 200 ppm) |
| $Co_3O_4$ | 450 | 0–200 ppm CO | 7 | 74 |
| $Co_3O_4$ | 450 | 0–500 ppm NO | 7 | 75 (to 200 ppm) |
| $Co_3O_4$ | 450 | 0–500 ppm $SO_2$ | 7 | 72 (to 200 ppm) |
| $Co_3O_4$ | 450 | 0–100 ppm $C_4H_{10}$ | 7 | 71 |
| $TiO_2$ | 450 | 0–500 ppm $NH_3$ | 5 | 53 (to 200 ppm) |
| $TiO_2$ | 450 | 0–200 ppm CO | 5 | 54 |
| $TiO_2$ | 450 | 0–500 ppm $SO_2$ | 5 | 52 (to 200 ppm) |
| $TiO_2$ | 450 | 0–100 ppm $C_4H_{10}$ | 5 | 51 |
| $V_2O_5$ | 450 | 0–500 ppm $NH_3$ | 6 | 63 (to 200 ppm) |

TABLE 5a-continued

Carrier Gas Measurement Side: 3% $O_2$ in $N_2$
Reference Gas: Surrounding Air

| Electrode Material | Temp. (Celsius) | Gas Component or Residual Concentration of Input Component in Carrier Gas of the Measurement Side to be Measured | Representation in FIG. NO. | Curve No. |
|---|---|---|---|---|
| $V_2O_5$ | 450 | 0–200 ppm CO | 6 | 64 |
| $V_2O_5$ | 450 | 0–100 ppm $SO_2$ | 6 | 62 |
| $V_2O_5$ | 450 | 0–100 ppm $C_4H_{10}$ | 6 | 61 |

TABLE 5b

Measurements with altered measurement side carrier stream composition

| Electrode Material | Temp. (Celsius) | Carrier Gas | Component | Representation in FIG. NO. | Curve No. |
|---|---|---|---|---|---|
| Pt.$V_2O_5$ | 450 | 3% $O_2$/$N_2$ 200 ppm NO, 200 ppm CO | 0–100 ppm $NH_3$ | 14 | 143/I |
| $Co_3O_4$ | 450 | $O_2$ | $O_3$(instat.) | 19 | 198 |
| $TiO_2$ | 450 | $O_2$ | $O_3$(instat.) | 19 | 197 |
| $V_2O_5$ | 450 | $O_2$ | $O_3$(instat.) | 19 | 196 |
| $Co_3O_4$ | 400 | $O_2$ | $O_3$(instat.) | 18 | 188 |
| $TiO_2$ | 400 | $O_2$ | $O_3$(instat.) | 18 | 187 |
| $V_2O_5$ | 400 | $O_2$ | $O_3$(instat.) | 18 | 186 |

"instat." means: injection of a $O_3$-containing gas volume into the flow.

EXAMPLE 14

To a gas mixture comprised of nitrogen and 3 percent-by-volume oxygen were added 0, 48, 102, 246, 380 and 574 ppm of Trichloroethane ($CCl_3CH_3$).

Figure 23:
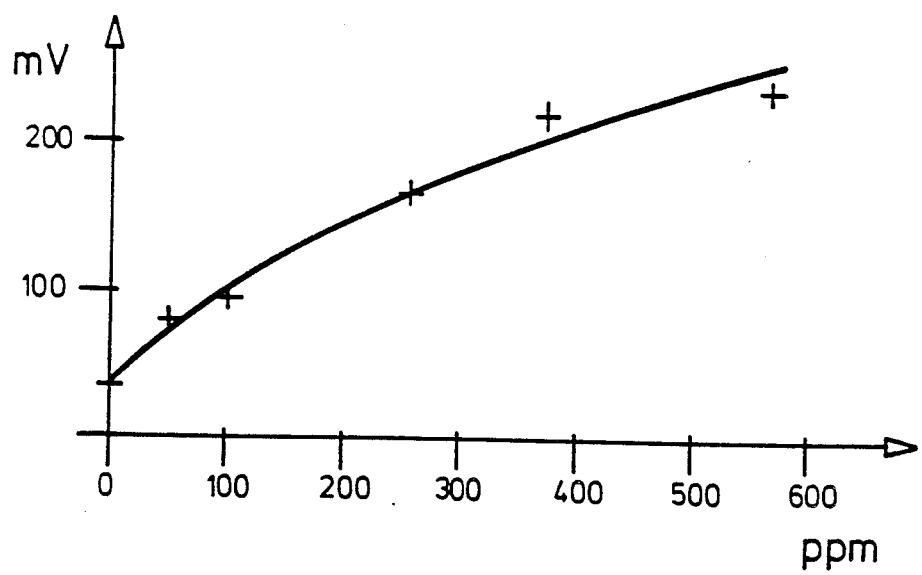

A sampling probe having an oxide electrode made of $V_2O_5$.$TiO_2$.Pt/$ZrO_2$($Y_2O_3$)/Pt was used to measure probe signals in mV at 450° C. for the $CCl_3CH_3$ component. As shown in FIG. 23, signals of 35, 80, 94, 164, 220 and 239 mV were obtained.

It will be understood that the above description of the present invention is susceptible to various modifications, changes and adaptations, and the same are intended to be comprehended within the meaning and range of equivalents of the appended claims.

What is claimed is:

1. Process for continuously monitoring the concentration of a gaseous component in a gas mixture, the mixture containing at least one of the gases CO, $NH_3$, $SO_2$, NO, $O_3$ and hydrocarbons and additionally containing oxygen in a known concentration, in which the gaseous component being monitored is not $O_2$, comprising:

(a) continuously generating and measuring electrical signals which are a function of the concentration of the gaseous component being monitored by bringing the gas mixture into contact with at least one electrochemical cell having at least one solid body which contains an oxygen-ion- conducting solid electrolyte material having a metal- oxide-containing electrode and generates electrical signals which are a function of the concentration of the component being monitored and (b) automatically and electronically evaluating the measured signals in a computer which converts the measured signals into concentration values and compares the converted values with reference values of a program which was earlier programmed into the computer.

2. Process according to claim 1, wherein the continuous measurement of the concentration of the gaseous component which is to be monitored or the measurement of the residual concentration of the gaseous component which is added, in order to avoid the disruptive influence of the measurement signal by means of further gas components, is carried out with an electrochemical cell which has no cross sensitivity with respect to the gas mixture components that are not measured.

3. Process according to claim 2, wherein measurement signal that is to be evaluated in the computer is a direct signal from a single electrochemical cell.

4. Process according to claim 1, wherein the continuous measurement of the concentration of the gaseous component which is to be monitored or the measurement of the residual concentration of the component which is added, in order to avoid the disruptive influence of the measurement signal by means of further gas components, is carried out with at least two electrochemical cells which are separated from one another and cross-connected with one another, and each of which has a measurement gas side, and wherein at least one of the cells contains a catalyst on the measurement gas side for chemically converting at least one gaseous component, and at least one of the cells does not have a catalyst on the measurement gas side, and the measurement signal that is to be evaluated in the computer, which corresponds to the concentration of the component which is to be monitored or to the residual concentration of the component which is added, is created by differential formation of the signal of the cell without a catalyst which corresponds to the sum concentration of all gas components, to the signal of the cell with a catalyst, which corresponds to the sum concentration of all gas components without the selectively chemically converted gas component.

5. Process according to claim 1, wherein the continuous measurement of the concentration of the gaseous component which is to be monitored or the measurement of the residual concentration of the component which is added, in order to avoid the disruptive influence of the measurement signal by means of further gas components, is carried out with an electrochemical cell which is in the form of at least two electrochemical partial cells, each of which has a measurement gas side, at least one of which partial cells contains a catalyst on the measurement gas side for chemically converting at least one gaseous component, and wherein the measurement signal that is to be evaluated in the computer, which corresponds to the concentration of the component which is to be monitored or to the residual concentration of the component which is added, is created by differential formation of the signal of the partial cell without a catalyst which corresponds to the sum concentration of all gas components, to the signal of the partial cell with a catalyst, which corresponds to the sum concentration of all gas components without the selectively chemically converted gas component.

6. The method according to claim 1, wherein the hydrocarbon is a chlorinated hydrocarbon.

7. Process for continuously monitoring and controlling the concentration of at least one gaseous component selected from the group CO, $NH_3$, $SO_2$, NO, $O_3$ and hydrocarbons in a gas mixture containing oxygen in a known concentration in which at least one gaseous component is fed into the gas mixture, whereby a portion of the gaseous component which is fed into the gas mixture is used up in a reaction with at least one other gaseous component comprising:

(a) continuously generating and measuring electrical signals which are the function of the residual concentration of the component which is added or of the concentration of the component that is to be monitored by bringing the gas mixture into contact with at least one electrochemical cell having at least one solid body which contains an oxygen-ion-conducting solid electrolyte material and contains a metal-oxide-containing electrode and which generates electrical signals which are a function of the residual concentration of the component which is added or of the concentration of the component to be monitored, (b) automatically and electronically evaluating the measured electrical signals in a computer which converts the measured signals into concentration values and compares the converted values with reference values of a program which was earlier programmed into the computer, and (c) automatically varying, by a signal from the computer, the amount of the component which is fed into the gas mixture in accordance with the level of differences between the converted values and the values of the program.

8. The method according to claim 7, wherein the hydrocarbon is a chlorinated hydrocarbon.

9. Apparatus for continuously monitoring the concentration of a gaseous component in a gas mixture, the mixture containing at least one of the gases CO, $NH_3$, $SO_2$, NO, $O_3$ and hydrocarbons and additionally containing oxygen in a known concentration, in which the gaseous compound being monitored is not $O_2$, comprising (1) a computer for automatically and electronically evaluating measure signals from a measurement unit, for converting the measured signals into concentration values, and for comparing the converted values with reference values of a program which was earlier programmed into the computer, and (2) a measurement unit which is comprised of a first gas sampling probe and a second gas sampling probe which is electrically connected to the first gas sampling probe, with each gas sampling probe having (i) a material that conducts oxygen ions and stays in contact with the measurement gas, with the material that conducts oxygen ions having a measurement gas side which has a surface that faces away from the measurement gas, (ii) an electrode mounted on the surface facing the measurement gas, (iii) an electrode mounted on the surface facing away from the measurement gas, (iv) and an electrical off-lead for transmitting measured signals that are generated in the measurement unit, wherein (a) each electrode on the surface which faces the measurement gas is a solid body structure,
(b) each solid body is made of metallic components and oxidic components or of oxidic components, and
(c) wherein a first set of electrical leads is mounted on the oxygen-ion-conducting material on the surface of each probe which faces the measurement gas, and a second set of electrical leads is mounted on the oxygen-ion-conducting material on the surface which is turned away from the measurement gas, and wherein the first set of electrical leads is connected to the computer to supply the computer with the measured signals, and the second set of electrical leads is joined together, and one of the probes has a gas-permeable catalyst layer which accelerates the chemical conversion of the gas component, the catalyst layer being on the side which faces the measurement gas and positioned above the solid electrode structure, and wherein the catalyst layer seals off the interstitial space to the oxygen-ion-conducting material and to the solid electrode body structure.

10. Apparatus according to claim 9, wherein the solid electrode body structure contains at least one oxide of at least one transition metal from the sub-groups IV, V, VIII and I of the periodic table of elements.

11. Apparatus according to claim 10, wherein the solid electrode body structure is made of one or more metals and of one or more oxides.

12. Apparatus according to claim 9, wherein the solid electrode body structure is made of one or more metals and of one or more oxides.

13. Apparatus according to claim 9, further comprising control means for controlling the amount of a gaseous component which is added to the gas mixture.

14. Apparatus for continuously monitoring the concentration of a gaseous component in a gas mixture, the mixture containing at least one of the gases CO, $NH_3$, $SO_2$, NO, $O_3$ and hydrocarbons and additionally containing oxygen in a known concentration, in which the gaseous compound being monitored is not $O_2$, comprising:

(1) a computer for automatically and electronically evaluating measured signals from a measurement unit, for converting the measured signals into concentration values, and for comparing the converted values with reference values to a program which was earlier programmed into the computer, and (2) a measurement unit which is comprised of at least one gas sampling probe having a material that conducts oxygen ions and stays in contact with the measurement gas, with the material that conducts oxygen ions having a measurement gas side which has a surface that faces away from the measurement gas, said probe having an element made of a material that does not conduct oxygen ions, which divides the oxygen-ion-conducting material into at least two parts, which are electrically connected to each other, with each part having (i) an electrode mounted on the surface facing the measurement gas, (ii) an electrode mounted on the surface facing away from the measurement gas, and (iii) an electrical off-lead for transmitting measured signals that are generated in the measurement, wherein (a) each electrode on the surface which faces the measurement gas is a solid body structure, (b) each solid body is made of metallic components and oxidic components or of oxidic components, and (c) wherein a first set of electrical leads is mounted on each part of the oxygen-ion-conducting material on the surface which faces the measurement gas, and a second set of electrical leads is mounted on each part of the oxygen-ion-conducting material on the surface which is turned away from the measurement gas, and wherein the first set of electrical leads is connected to the computer to supply the computer with the measured signals, and the second set of electrical leads is joined together, wherein a catalyst layer which accelerates the chemical transformation of a gas component is positioned on the side which faces the measurement gas, and is positioned above at least one part of the material which is conducting a portion of the oxygen ions, above the solid electrode body structure, and wherein the catalyst layer is arranged to close off the interstitial space to the oxygen-ion-conducting material and to the solid electrode body structure.

15. Apparatus according to claim 14, wherein the solid electrode body structure contains at least one oxide of at least one transition metal from the sub-groups IV, V, VIII and I of the periodic table of elements.

16. Apparatus according to claim 15, wherein the solid electrode body structure is made of one or more metals and of one or more oxides.

17. Apparatus according to claim 14, wherein the solid electrode body structure is made of one or more metals and of one or more oxides.

18. Apparatus according to claim 14, further comprising control means for controlling the amount of a gaseous component which is added to the gas mixture.

* * * * *